US010406032B2

(12) United States Patent
Gooding et al.

(10) Patent No.: US 10,406,032 B2
(45) Date of Patent: Sep. 10, 2019

(54) LIQUID LOSS DETECTION DURING LASER EYE SURGERY

(71) Applicant: OPTIMEDICA CORPORATION, Sunnyvale, CA (US)

(72) Inventors: Phillip H. Gooding, Mountain View, CA (US); Christine J. Beltran, Sunnyvale, CA (US); Brent Eikanas, Brentwood, CA (US); Michael A. Campos, Fremont, CA (US)

(73) Assignee: OPTIMEDICA CORPORATION, Santa Ana, CA (US)

( * ) Notice: Subject to any disclaimer, the term of this patent is extended or adjusted under 35 U.S.C. 154(b) by 729 days.

(21) Appl. No.: 14/970,789

(22) Filed: Dec. 16, 2015

(65) Prior Publication Data
US 2016/0175146 A1 Jun. 23, 2016

Related U.S. Application Data

(60) Provisional application No. 62/094,788, filed on Dec. 19, 2014.

(51) Int. Cl.
A61F 9/009 (2006.01)
A61F 9/008 (2006.01)

(52) U.S. Cl.
CPC .............. A61F 9/008 (2013.01); A61F 9/009 (2013.01); A61F 9/00825 (2013.01)

(58) Field of Classification Search
CPC ....... A61F 9/008; A61F 9/009; A61F 9/00825
USPC .......................................................... 606/4
See application file for complete search history.

(56) References Cited

U.S. PATENT DOCUMENTS

| 5,656,027 | A | 8/1997 | Ellingboe |
| 5,720,894 | A | 2/1998 | Neev et al. |
| 5,957,915 | A | 9/1999 | Trost |
| 5,984,916 | A | 11/1999 | Lai |
| 6,019,472 | A | 2/2000 | Koester et al. |
| 6,454,761 | B1 | 9/2002 | Freedman |
| 7,655,002 | B2 | 2/2010 | Myers et al. |
| 7,717,907 | B2 | 5/2010 | Ruiz et al. |
| 8,262,646 | B2 | 9/2012 | Frey et al. |
| 8,350,183 | B2 | 1/2013 | Vogel et al. |
| 8,382,745 | B2 | 2/2013 | Naranjo-Tackman et al. |
| 8,394,084 | B2 | 3/2013 | Blumenkranz et al. |
| 8,414,564 | B2 | 4/2013 | Goldshleger et al. |
| 8,425,497 | B2 | 4/2013 | Blumenkranz et al. |

(Continued)

OTHER PUBLICATIONS

International Search Report and Written Opinion for Application No. PCT/US2015/065979, dated Mar. 29, 2016, 13 pages.

Primary Examiner — Aaron F Roane
(74) Attorney, Agent, or Firm — Johnson & Johnson Surgical Vision, Inc.

(57) ABSTRACT

A laser eye surgery system that has a patient interface between the eye and the laser system relying on suction to hold the interface to the eye, the patient interface using liquid used as a transmission medium for the laser. During a laser procedure sensors monitor the level of liquid within the patient interface and send a signal to control electronics if the level drops below a threshold value. The sensor may be mounted on the inside of the patient interface, within a fluid chamber. Alternatively, a gas flow meter may be added to a suction circuit for the patient interface that detects abnormal suction levels indicating low fluid level.

20 Claims, 10 Drawing Sheets

(56) References Cited

U.S. PATENT DOCUMENTS

| | | |
|---|---|---|
| 8,500,724 B2 | 8/2013 | Blumenkranz et al. |
| 2011/0319873 A1 | 12/2011 | Raksi et al. |
| 2011/0319875 A1 | 12/2011 | Loesel et al. |
| 2013/0102922 A1 | 4/2013 | Gooding et al. |
| 2013/0338649 A1 | 12/2013 | Hanebuchi et al. |
| 2014/0012821 A1 | 1/2014 | Fuhrmann et al. |
| 2014/0128821 A1 | 5/2014 | Gooding et al. |
| 2014/0128853 A1* | 5/2014 | Angeley ............. A61F 9/00827 606/4 |
| 2014/0163534 A1* | 6/2014 | Angeley ............. A61F 9/00825 606/4 |
| 2014/0343541 A1 | 11/2014 | Scott et al. |
| 2015/0018674 A1 | 1/2015 | Scott et al. |
| 2015/0190278 A1* | 7/2015 | Gooding ................ A61F 9/009 606/4 |

\* cited by examiner

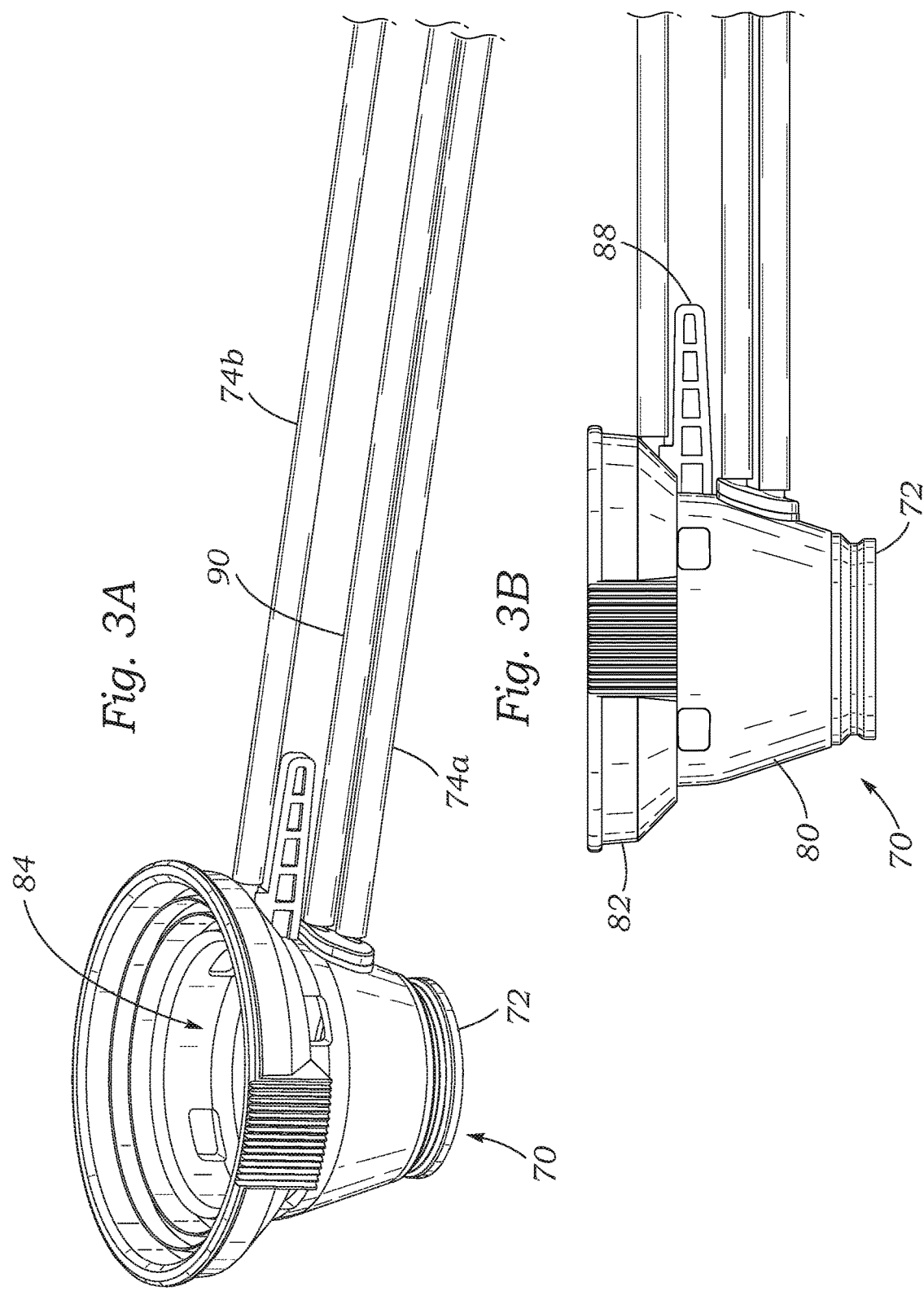

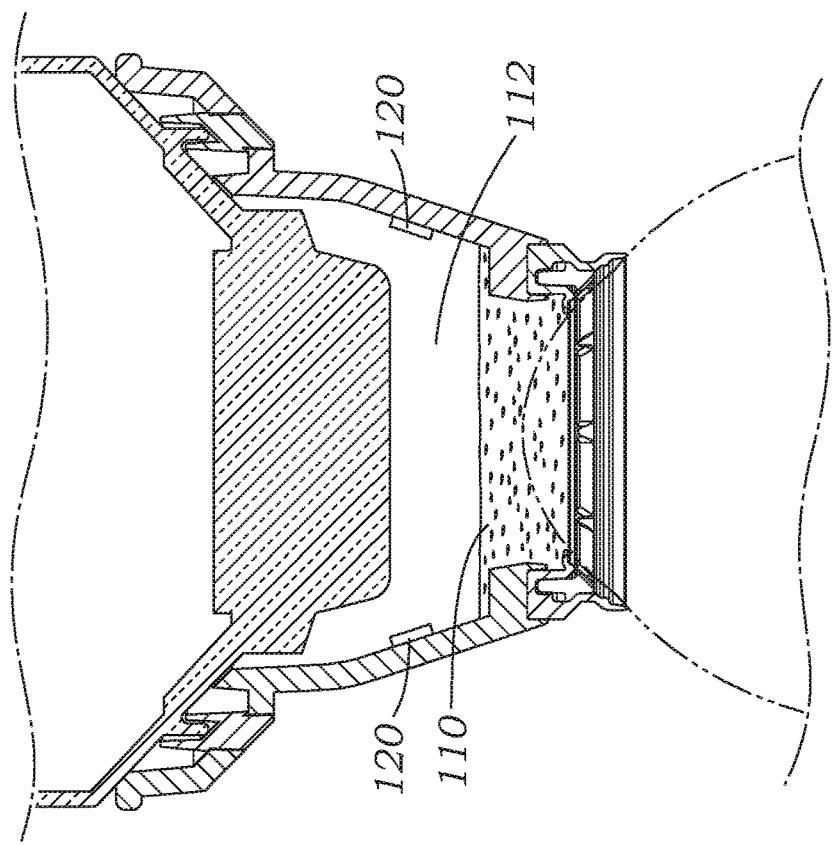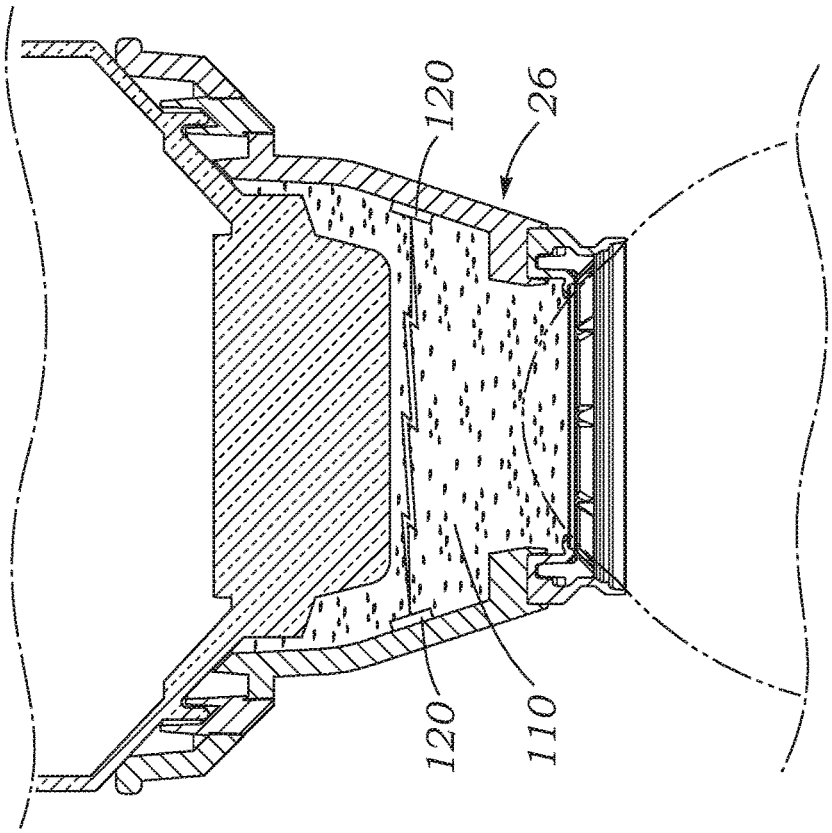

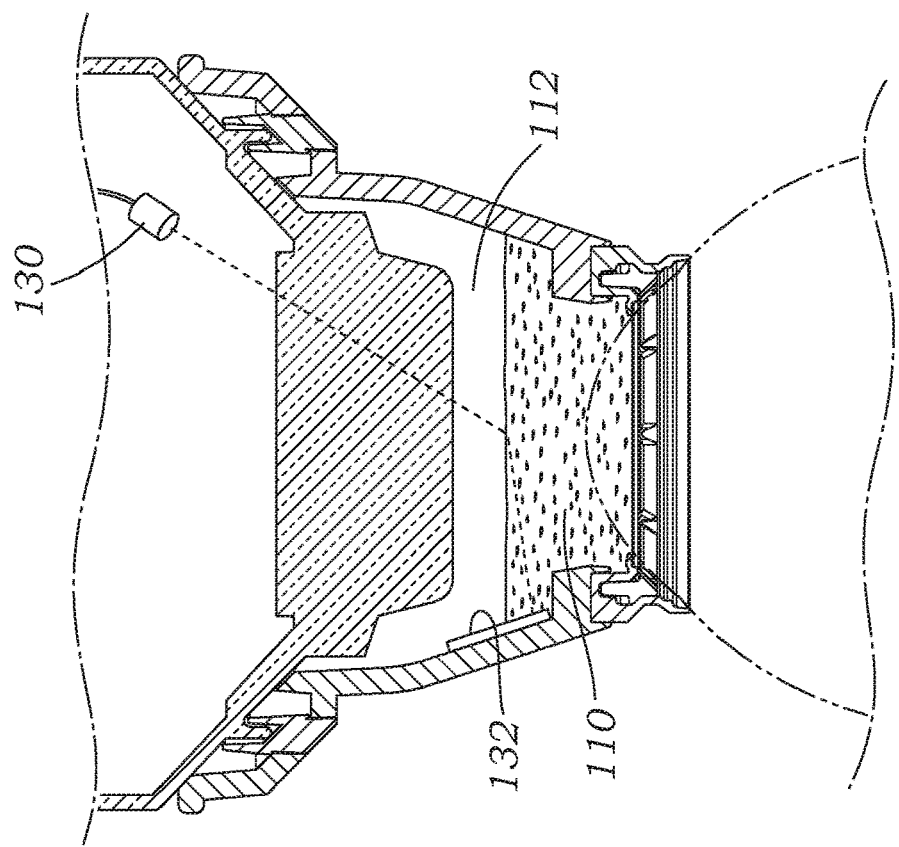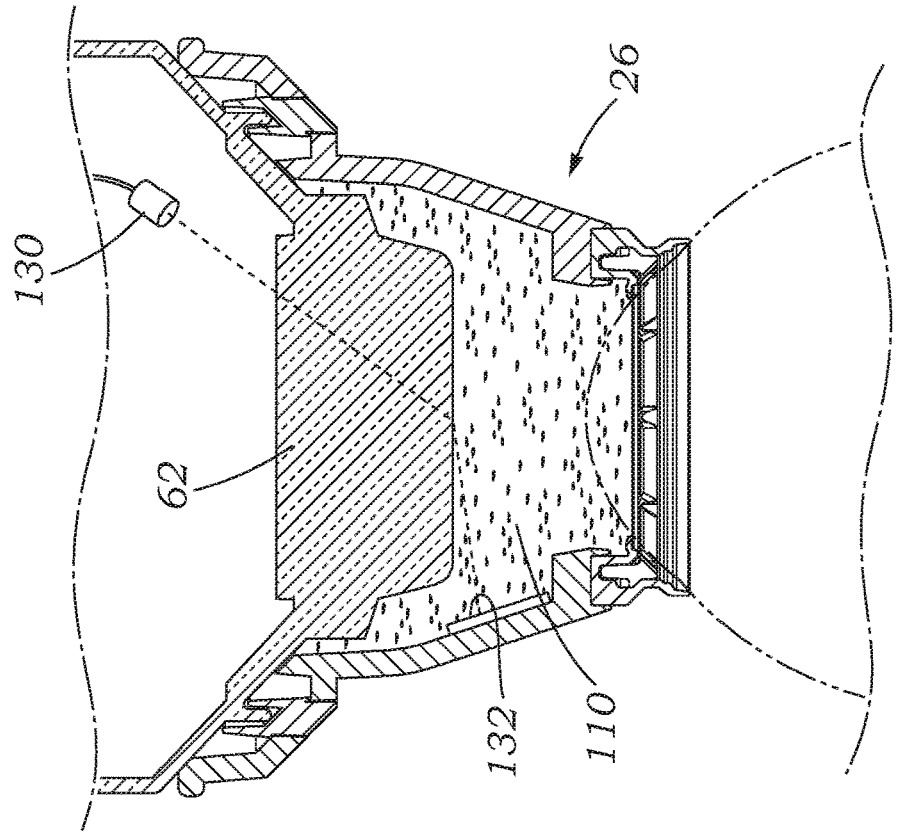

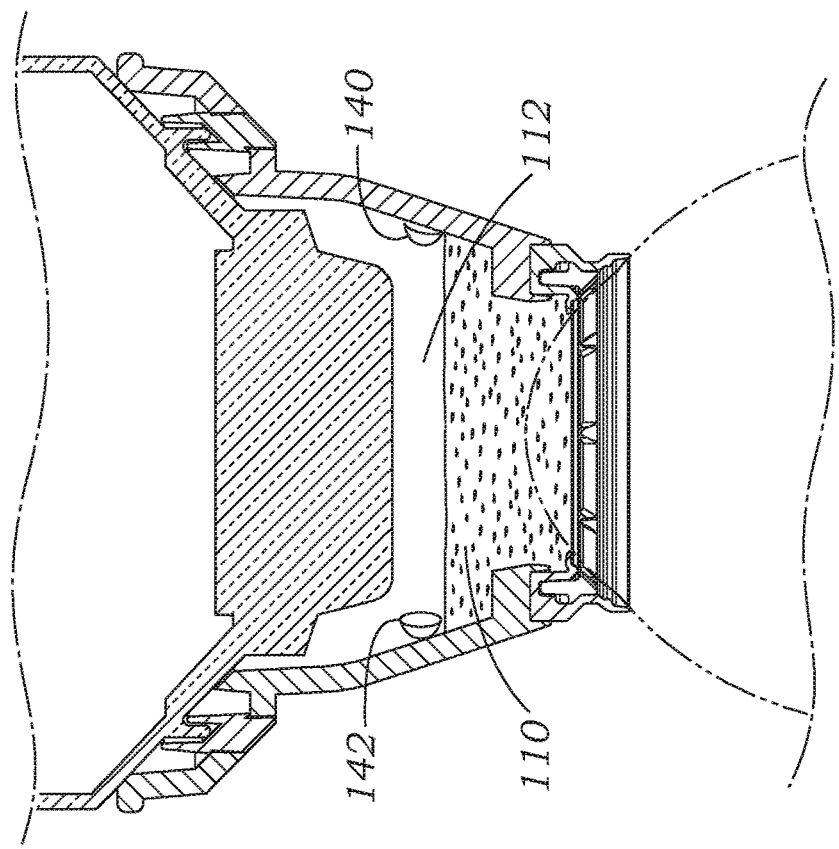
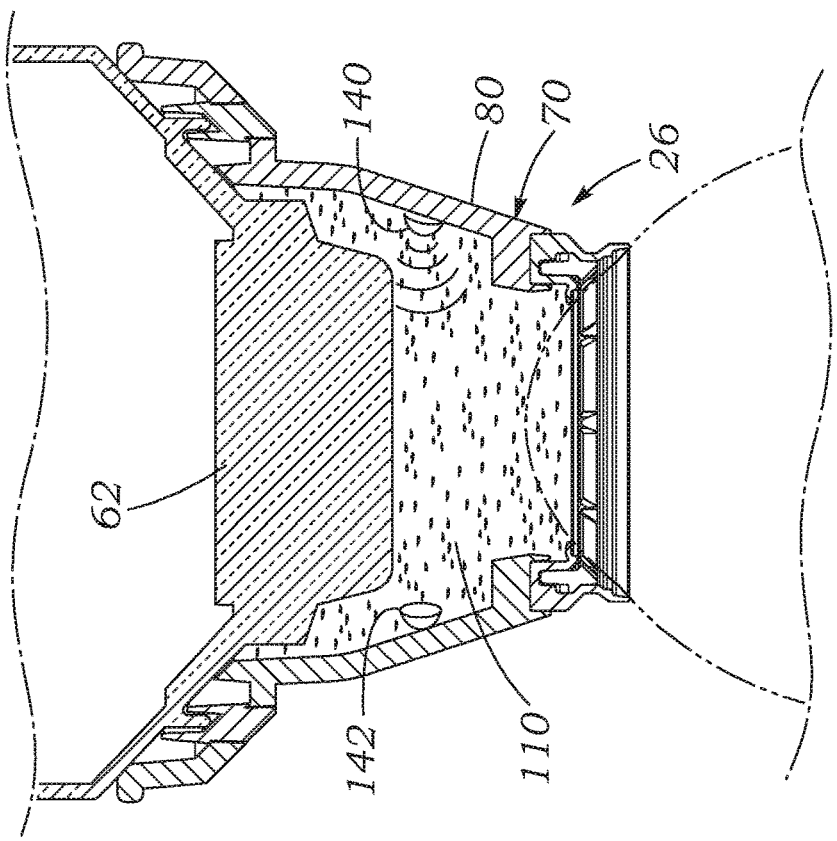

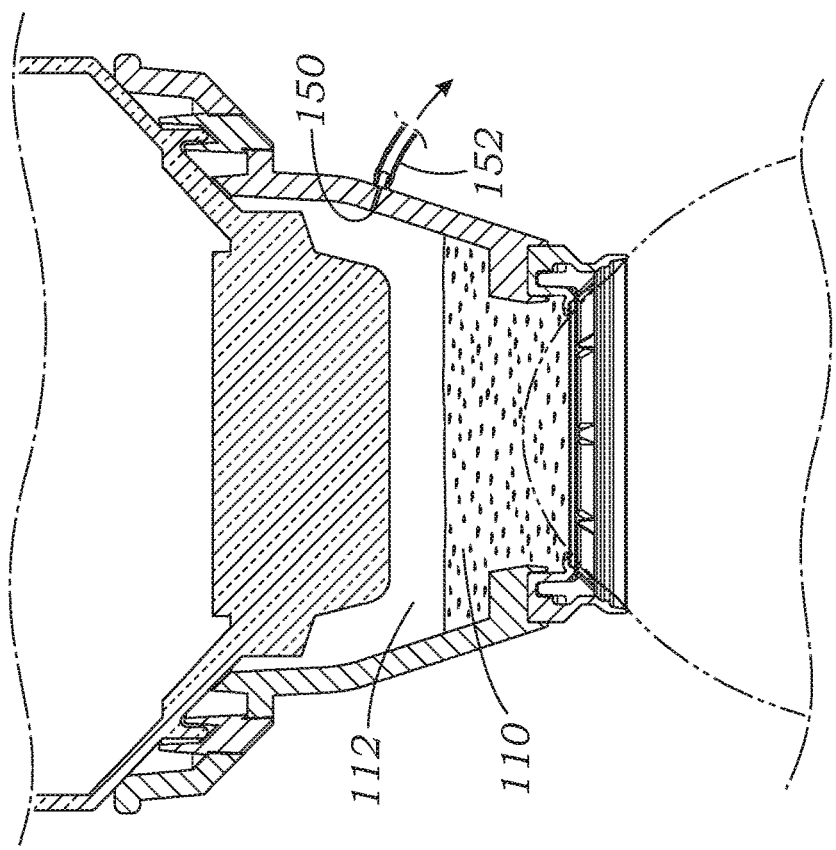
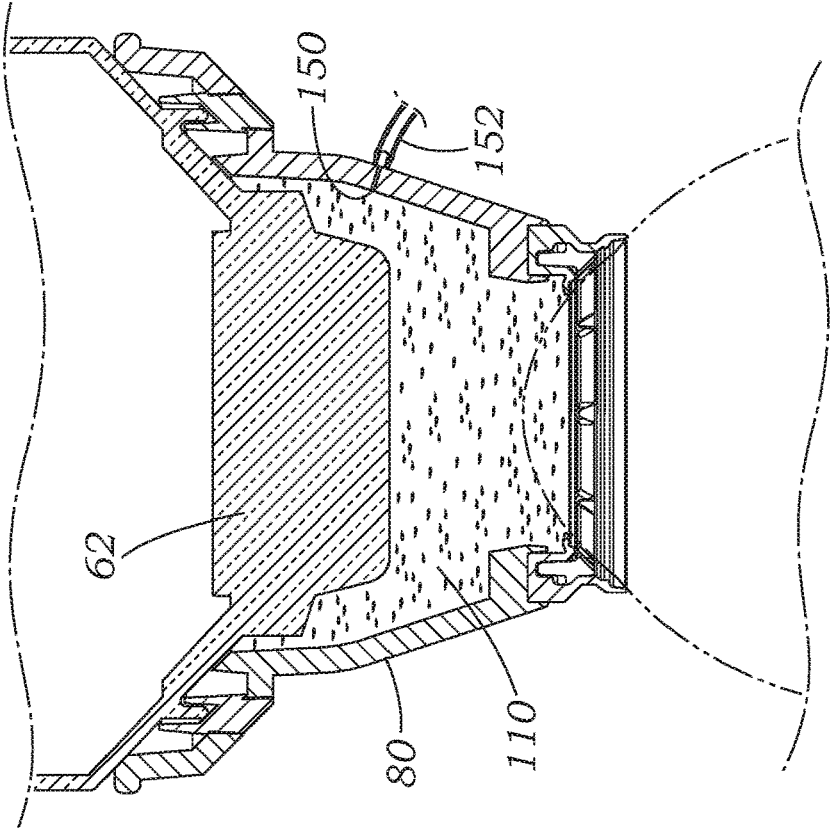

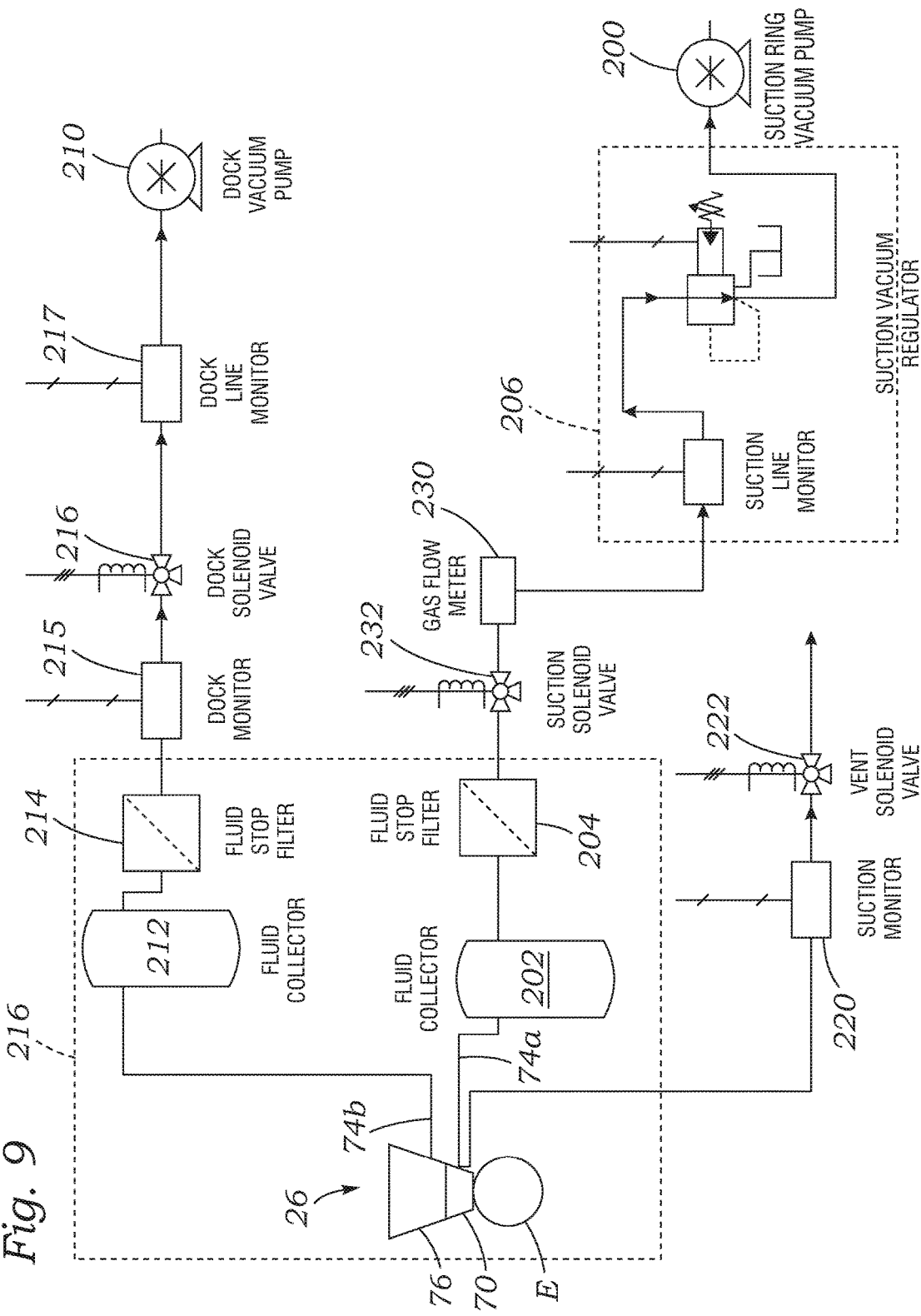

LIQUID LOSS DETECTION DURING LASER EYE SURGERY

RELATED APPLICATIONS

This application is a non-provisional application and claims the benefit under 35 U.S.C. § 119(e) of U.S. Provisional Application Ser. No. 62/094,788, filed Dec. 19, 2014, which is incorporated herein in its entirety by reference.

FIELD OF THE INVENTION

The present application pertains to laser-assisted eye surgery using a liquid optical interface and, more particularly, to systems and methods for monitoring and reacting to insufficient liquid within the interface.

BACKGROUND

A cataract is formed by opacification of the crystalline lens or its envelope—the lens capsule—of the eye. The cataract obstructs passage of light through the lens. A cataract can vary in degree from slight to complete opacity. Early in the development of an age-related cataract, the power of the lens may be increased, causing near-sightedness (myopia). Gradual yellowing and opacification of the lens may reduce the perception of blue colors as those wavelengths are absorbed and scattered within the crystalline lens. Cataract formation typically progresses slowly resulting in progressive vision loss. If left untreated, cataracts may cause blindness.

A common cataract treatment involves replacing the opaque crystalline lens with an artificial intraocular lens (IOL). Every year, an estimated 15 million cataract surgeries are performed worldwide. Traditionally, cataract surgery has been typically performed using a technique called phacoemulsification in which an ultrasonic tip with associated irrigation and aspiration ports is used to sculpt the relatively hard nucleus of the lens to facilitate removal through an opening made in the anterior lens capsule. Access to the lens nucleus can be provided by performing an anterior capsulotomy in which a small round hole is formed in the anterior side of the lens capsule using a surgical. Access to the lens nucleus can also be provided by performing a manual continuous curvilinear capsulorhexis (CCC) procedure. After removal of the lens nucleus, a synthetic foldable intraocular lens (IOL) can be inserted into the remaining lens capsule of the eye.

One of the most technically challenging and critical steps in the cataract extraction procedure is providing access to the lens nucleus for removal of the cataract by phacoemulsification. The desired outcome is to provide a smooth continuous circular opening through which phacoemulsification of the nucleus can be performed safely and easily, and also through which an intraocular lens may be easily inserted. Because of the criticality of this step, some surgeons prefer a surgical laser beam over manual tools like microkeratomes and forceps since the laser beam can be focused precisely on extremely small amounts of eye tissue, thereby enhancing the accuracy and reliability of the capsulotomy procedure.

Several commercial laser-assisted eye surgery systems are available to facilitate cataract removal and astigmatism correction. The CATALYS Precision Laser System from Abbott Medical Optics is indicated for anterior capsulotomy, phacofragmentation, and the creation of single plane and multi-plane arc cuts/incisions in the cornea to correct astigmatism. The CATALYS System uses a two-piece liquid-filled interface that docks with the patient's eye with the liquid providing a transmission medium for the laser, thus avoiding distortion of the eye from contact with an applanation lens. The liquid provides a clear optical path for real-time video, OCT imaging, and laser treatment. Aspects of the CATALYS System are disclosed in U.S. Pat. Nos. 8,394,084, 8,500,724, 8,425,497, U.S. Patent Publication 2014/0163534, U.S. patent application Ser. No. 14/256,307, filed Apr. 18, 2014, and U.S. Patent Publication No. 2014/0343541, filed Apr. 17, 2014, the contents of all of which are incorporated herein by reference as if fully set forth. Other systems for laser cataract surgery are the LenSx Laser from Alcon Laboratories, Inc., the LENSAR Laser System from LENSAR, Inc., and the VICTUS Femtosecond Laser Platform from TECHNOLAS Perfect Vision GmbH a Bausch+Lomb Company.

The interstitial layer of fluid has a strong influence on the delivery of a high fidelity laser spot in the correct location. One drawback with current systems that use liquid-filled optical interfaces is loss of liquid. Most docking interfaces rely on suction to hold the interface to the eye, and sometimes to hold separate pieces of the interface together. If during a laser procedure the interface shifts so that the liquid-filled chamber comes in fluid communication with the suction in any of these couplings, the level of liquid in the interface may be reduced to be replaced with air which has a different index of refraction and would affect the laser optics. If this happens during laser treatment, it is important to shut off delivery of the laser energy before any mistreatment, or even injury, can occur.

Accordingly, there is a need for systems that detect loss of liquid in the optical interface.

SUMMARY

Improved laser eye surgery systems, and related methods, are provided. The laser eye surgery systems use a laser to form precise incisions in the cornea, in the lens capsule, and/or in the crystalline lens nucleus. In a preferred embodiment, a laser eye surgery system includes a laser cutting subsystem to produce a laser pulse treatment beam to incise tissue within the eye. A liquid transmissive media is used between a patient interface lens and the eye to avoid imparting undesirable forces to the patient's eye. The present application provides a number of solutions for monitoring the liquid level within the patient interface.

One particular embodiment of a liquid monitor includes one or more sensors positioned within the patient interface and in communication with the liquid therein. The sensors may be conductive pads which conduct current therebetween through the liquid until the liquid level drops too low. Alternatively, a light source may be shone down onto the liquid within the patient interface and light refracted through the liquid monitored for changes in the liquid level. Still further, a matched pair of acoustic emitter and sensor may be integrated into the patient interface which produce different signals when the liquid levels are high and low. Another solution is to incorporate an extremely small diameter orifice in the side of the liquid chamber and pull a very low vacuum on the orifice. If the liquid is covering the orifice, surface tension will prevent aspiration of the fluid, but when the liquid level drops air can be pulled through the orifice which is detected by an external sensor in the vacuum line. Finally, a gas flow meter may be installed within a vacuum supply circuit for a suction ring on the patient interface. The gas flow meter detects major suction losses as well as slow leaks by utilizing a sensor of high sensitivity.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 3A-3D are perspective, elevational, plan and sectional views, respectively, of an eye-contacting member of an exemplary patient interface of the present application;

FIGS. 5A and 5B are sectional views through the assembled patient interface taken along a section line perpendicular to that of FIG. 4 and showing a first solution for monitoring a fluid level within the interface comprising conductive pads mounted to an inner wall of the eye-contacting member with the fluid level both high and low, respectively;

FIGS. 6A and 6B are sectional views through the assembled patient interface showing another solution for monitoring the fluid level including a light source and refracted light position detector integrated into the interface;

FIGS. 7A and 7B are sectional views through the assembled patient interface showing a still further solution for monitoring the fluid level including a matched pair of acoustic emitter and sensor integrated within the interface;

FIGS. 8A and 8B are sectional views through the assembled patient interface showing yet another solution for monitoring a fluid level including a small orifice through the wall of the interface connected to a vacuum line; and FIG. 9 is a schematic of suction circuits connected to the patient interface and showing a still further solution for monitoring a fluid level within the patient interface.

DETAILED DESCRIPTION

Methods and systems related to laser eye surgery are disclosed. A laser is used to form precise incisions in the cornea, in the lens capsule, and/or in the crystalline lens nucleus. In a preferred embodiment, a laser eye surgery system includes a laser cutting subsystem to produce a laser pulse treatment beam to incise tissue within the eye, a ranging subsystem to measure the spatial disposition of external and internal structures of the eye in which incisions can be formed, an alignment subsystem, and shared optics operable to scan the treatment beam, a ranging subsystem beam, and/or an alignment beam relative to the laser eye surgery system. The alignment subsystem can include a video subsystem that can be used to, for example, provide images of the eye during docking of the eye to the laser eye surgery system and also provide images of the eye once the docking process is complete. In a preferred embodiment, a liquid interface is used between a patient interface lens and the eye. The use of the liquid interface avoids imparting undesirable forces to the patient's eye.

Laser System Configuration

Figure 1:
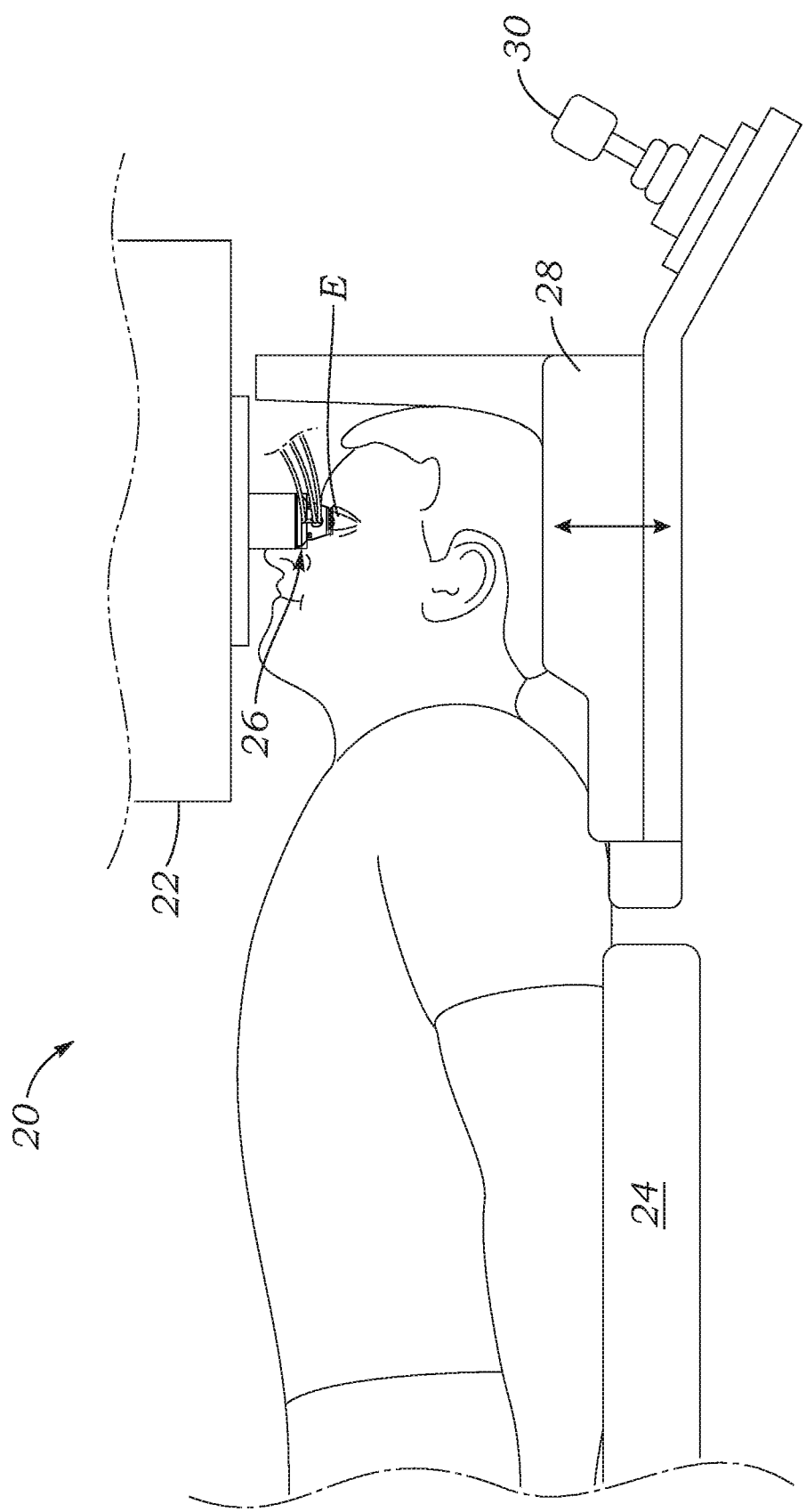
FIG. 1 is a side view of a patient positioned under a patient interface of a laser-assisted eye surgery system.

FIG. 1 shows a laser eye surgery system 20, in accordance with the present application, operable to form precise incisions in the cornea, in the lens capsule, and/or in the crystalline lens nucleus. The system 20 includes a diagnostic and interventional unit 22 under which the patient lies on a patient chair 24 that may be elevated up and down. A patient interface 26 is shown between the eye E of the patient and the diagnostic and interventional unit 22, the attributes of which will be described below.

The diagnostic and interventional unit 22 houses a number of subsystems which are not illustrated herein. For example, the unit 22 may provide a touch-screen control panel, patient interface vacuum connections, a docking control keypad, a patient interface radio frequency identification (RFID) reader, external connections (e.g., network, video output, one or more foot switches, USB port, door interlock, and AC power), a laser emission indicator, an emergency laser stop button, key switch, and USB data ports. These subsystems are shown and described in U.S. Patent Publication No. 2014/012821, filed Oct. 31, 2013, the contents of which are expressly incorporated herein by reference.

The patient chair 24 includes a headrest 28 and a patient chair joystick control 30 for a chair positioning mechanism (internal, not shown). The patient chair 24 is configured to be adjusted and oriented in three axes (x, y, and z) using the patient chair joystick control 30. The headrest 28 and a restrain system (not shown, e.g., a restraint strap engaging the patient's forehead) stabilize the patient's head during the procedure. The headrest 28 desirably includes an adjustable neck support to provide patient comfort and to reduce patient head movement. The headrest 28 is configured to be vertically adjustable to enable adjustment of the patient head position to provide patient comfort and to accommodate variation in patient head size.

The patient chair 24 allows for tilt articulation of the patient's legs, torso, and head using manual adjustments. The patient chair 24 accommodates a patient load position, a suction ring capture position, and a patient treat position. In the patient load position, the chair 24 is rotated out from under the diagnostic and interventional unit 22 with the patient chair back in an upright position and patient footrest in a lowered position. In the suction ring capture position, the chair is rotated out from under the diagnostic and interventional unit 22 with the patient chair back in reclined position and patient footrest in raised position. In the patient treat position, the chair is rotated under the diagnostic and interventional unit 22 with the patient chair back in reclined position and patient footrest in raised position.

Figure 2:
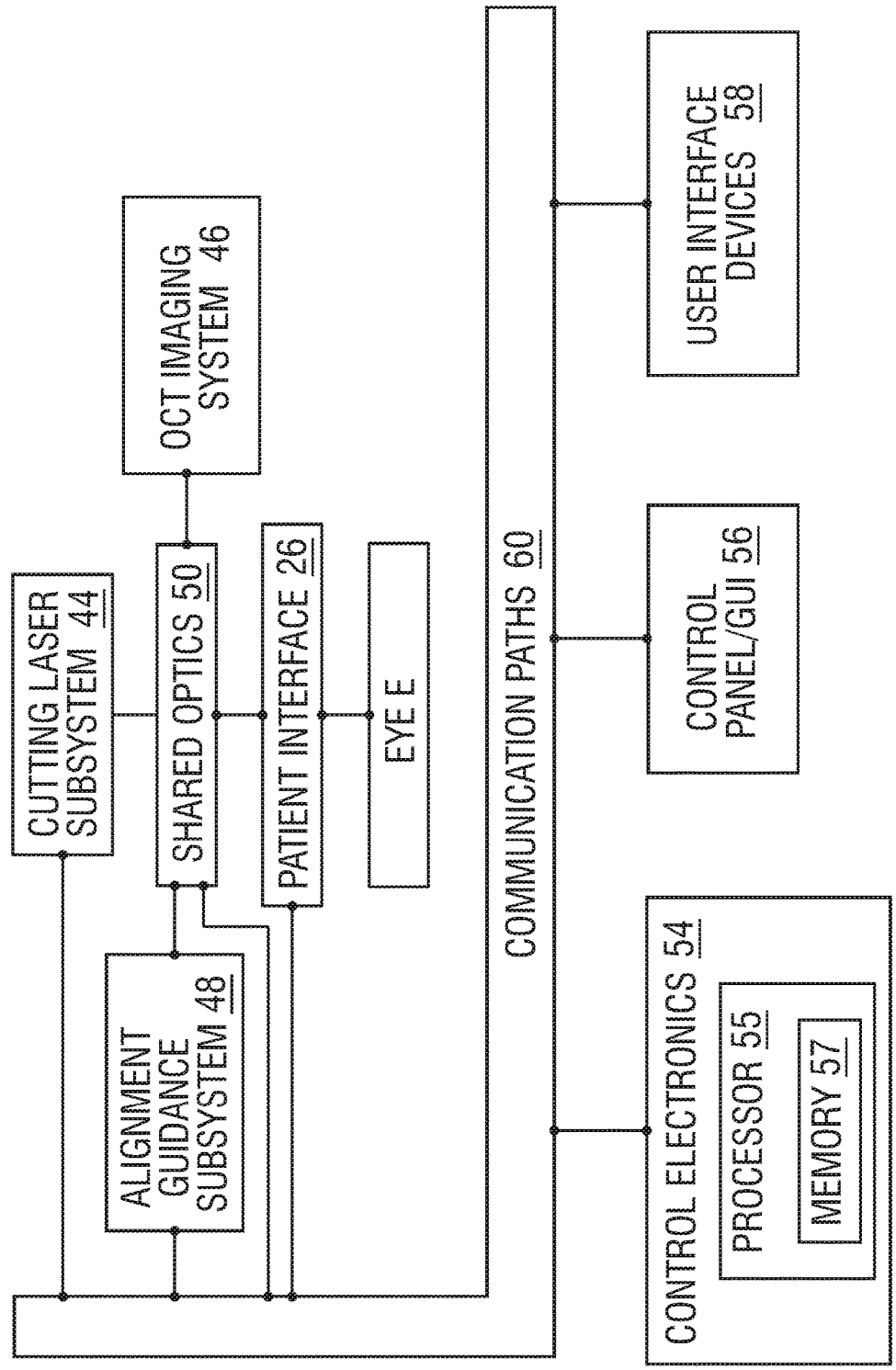
FIG. 2 is a simplified block diagram showing a top level view of the configuration of a laser eye surgery system having a patient interface in accordance with the present application.

FIG. 2 shows a simplified block diagram of the system 20 coupled with a patient eye E. The patient eye E comprises a cornea, a lens, and an iris. The iris defines a pupil of the eye E that may be used for alignment of eye E with system 20. The system 20 includes a cutting laser subsystem 44, an OCT imaging system 46, an alignment guidance system 48, a video camera 49, shared optics 50, the patient interface 26, control electronics 54, a control panel/GUI 56, user interface devices 58, and communication paths 60. The control electronics 54 are operatively coupled via the communication paths 60 with the cutting laser subsystem 44, the OCT imaging system 46, the alignment guidance subsystem 48, the video camera 49, the shared optics 50, the patient interface 26, the control panel/GUI 56, and the user interface devices 58. Again, further details of these aspects are shown and described in U.S. Patent Publication No. 2014/012821, to Gooding, previously incorporated herein by reference.

In a preferred embodiment, the cutting laser subsystem 44 may incorporates femtosecond (FS) laser technology. By using femtosecond laser technology, a short duration (e.g., approximately $10^{-13}$ seconds in duration) laser pulse (with energy level in the micro joule range) can be delivered to a tightly focused point to disrupt tissue, thereby substantially lowering the energy level required as compared to the level required for ultrasound fragmentation of the lens nucleus and as compared to laser pulses having longer durations. The cutting laser subsystem 44 can produce laser pulses having a wavelength suitable to the configuration of the system 20. As a non-limiting example, the system 20 can be configured to use a cutting laser subsystem 44 that produces laser pulses having a wavelength from 1020 nm to 1050 nm. For example, the cutting laser subsystem 44 can have a diode-pumped solid-state configuration with a 1030 (+/−5) nm center wavelength.

Patient Interfaces

The patient interface 26 is used to restrain the position of the patient's eye E relative to the system 20. In a preferred embodiment, the patient interface 26 employs a suction ring that attaches to the patient's eye E using a vacuum line. The suction ring is then coupled with the patient interface 26, for example, using vacuum to secure the suction ring to the patient interface 26. In a preferred embodiment, the patient interface 26 includes an optically transmissive structure (lens) having a posterior surface that is displaced vertically from the anterior surface of the patient's cornea and a region of a suitable liquid (e.g., a sterile buffered saline solution (BSS)) is disposed between and in contact with the posterior surface and the patient's cornea to form part of a transmission path between the shared optics 50 and the patient's eye E. The optically transmissive structure may comprise a lens 62 (see FIG. 4) having one or more curved surfaces. Alternatively, the patient interface 26 may comprise an optically transmissive structure having one or more substantially flat surfaces such as a parallel plate or wedge. In a preferred embodiment, the patient interface lens is disposable and is replaced before each eye treatment.

FIGS. 3A-3D depict an eye-contacting member 70 of the exemplary patient interface 26 used in the laser eye surgery systems described herein. As mentioned above, an exemplary patient interface 26 incorporates a suction ring 72 for coupling with the eye E, for example, using vacuum. More specifically, a lower or distal end of the patient interface 26 is placed in contact with the cornea of the eye E and suction drawn through a first suction conduit 74a coupled to the suction ring. The first suction conduit 74a extends from the suction ring 72 to a plurality of components including a vacuum source, as will be described with reference to FIG. 9.

The patient interface 26 comprises a two-part assembly with an upper member 76 (see FIG. 4) having features configured to be removably coupled to the diagnostic and interventional unit 22, such as that described above in reference to FIG. 1. The upper member 76 is also removably coupled to the eye-contacting member 70 via suction, as will be described. In an exemplary procedure, the patient chair 24 is rotated out from under the diagnostic and interventional unit 22 to the suction ring capture position. A physician or technician can then easily engage the eye-contacting member 70 of the interface 26 to the patient's eyes E using the suction ring 72. The chair 24 is then rotated to the patient treat position under the diagnostic and interventional unit 22, and the eye-contacting member 70 and upper member 76 are coupled together, such as shown in FIG. 1. The system 20 is then ready for a laser-assisted ophthalmic procedure.

It should be noted that the patient interface 26 may comprise separable components such as the eye-contacting member 70 and upper member 76, or can be provided together as a single inseparable unit. Further details of exemplary liquid-filled patient interfaces are disclosed in U.S. Patent Publication 2013/0102922, filed Oct. 21, 2011, the contents of which are expressly incorporated herein by reference.

With reference again to FIGS. 3A-3D, the eye-contacting member 70 of the patient interface 26 in this embodiment comprises a generally frustoconical body 80 having an upper cylindrical rim 82. The rigid, preferably molded, body 80 has a generally annular cross-section and defines therein a throughbore 84 as seen best in FIG. 3D. A small radially-projecting handle 88 permits a physician or technician to easily manipulate the member 70, and a trio of fluid conduits 74a, 74b and 90 extend radially away in the same direction.

Figure 3C:
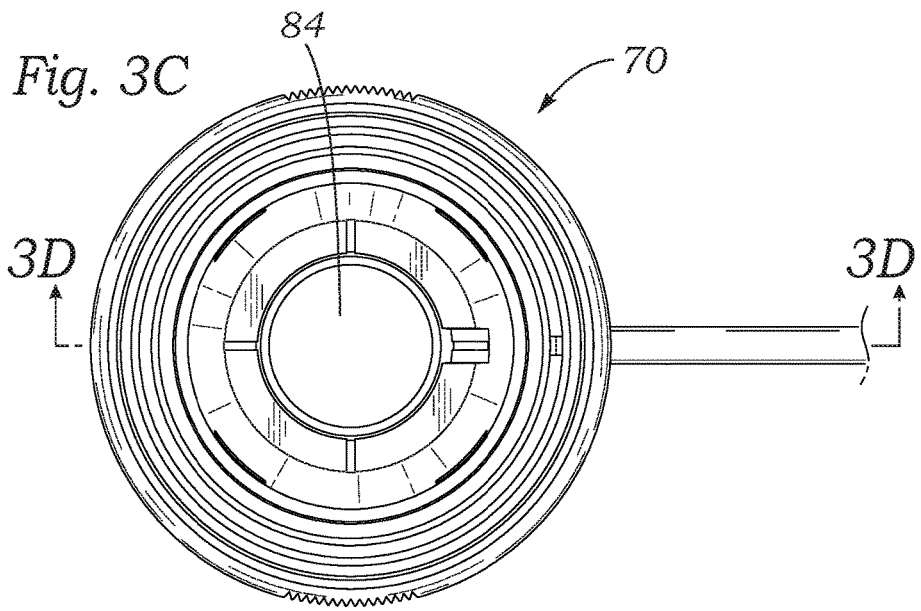
Figure 3D:
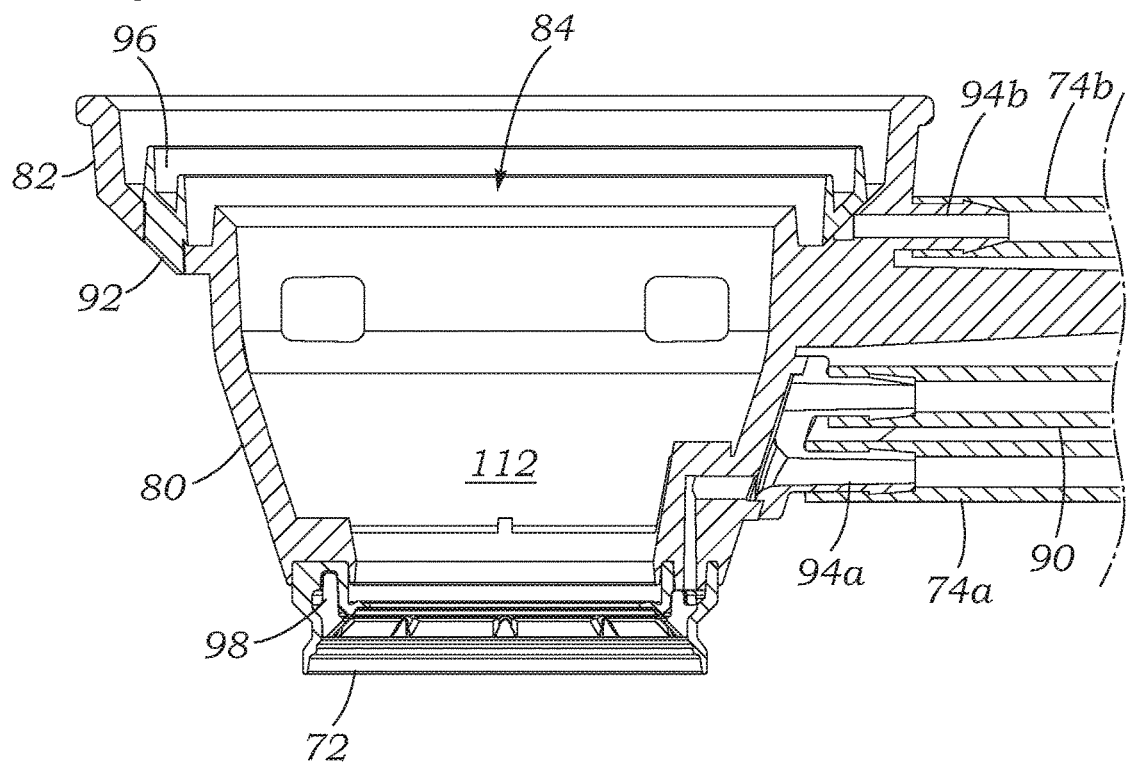

FIG. 3D best shows an internal structure of the eye-contact member 70. The body 80 receives an annular elastomeric seal 92 in a circular groove to provide a seal for mating with the upper member 76. The upper fluid conduit 74b attaches to a corresponding nipple 94b having a lumen that is in fluid communication with an annular space 96 defined within two walls of the seal 92. As is shown in FIG. 4, a vacuum pulled through the conduit 74b creates a suction within the seal 92 which pulls a lower surface of the upper member 76 into contact with the seal, thus effectively holding together the two parts of the patient interface 26.

On the bottom end of the frustoconical body 80, the elastomeric suction ring 72 also defines a pair of annular walls (not numbered) that define a space 98 therebetween. The lower fluid conduit 74a attaches to a corresponding nipple 94a having a lumen that is in fluid communication with the space 98. When a vacuum is pulled through the conduit 74a, the suction ring 72 can be secured to the generally spherical surface of the eye E.

Figure 4:
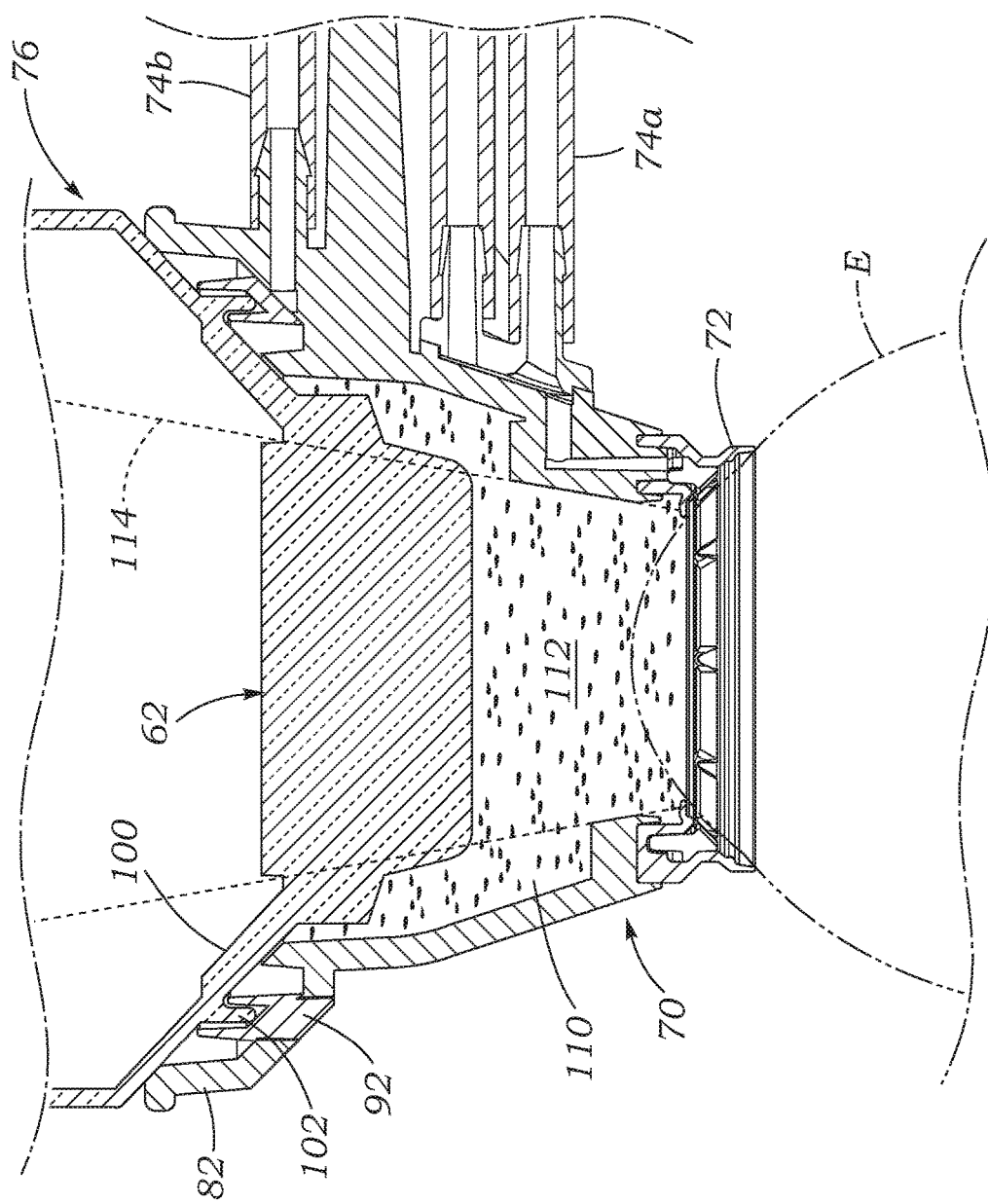
FIG. 4 is a sectional view through an assembled patient interface with the eye-contacting member docked against an upper member that has an object lens for laser delivery.

The assembly of the eye-contacting member 70 coupled to the eye E, with the upper member 76 held by suction to the elastomeric seal 92, is shown in FIG. 4. As mentioned above, the upper member 76 mounts within the upper cylindrical rim 82 of the frustoconical body 80 of the eye-contacting member 70. The upper member 76 includes a generally frustoconical wall 100 having a small circular flange 102 projecting downward therefrom that fits within the annular space 96 (FIG. 3D) defined within the two walls of the elastomeric seal 92. This helps center the two components. A vacuum through the upper fluid conduit 74b pulls the frustoconical wall 100 against the blades of the elastomeric seal 92, thus securing the upper member 76 to the eye-contacting member 70.

The optical lens 62 is thus held securely centered within the patient interface 26, and above the eye E. More specifically, the posterior surface of the optical lens 62 is spaced vertically from the anterior surface of the patient's cornea across a region of a suitable liquid 110 (e.g., a sterile buffered saline solution (BSS)) within a transmissive fluid chamber 112. The chamber 112 includes that portion of the throughbore 84 within the eye-contacting member 70 below the lens 62 and within a conical field of view 114 (shown in dashed line) of the optical instruments of the laser-assisted system described above. However, the chamber 112 also extends outward from the field of view 114 which provides space for the liquid level sensing instruments described herein. Although not shown, inlet and outlet ports to the chamber 112 are provided in the eye-contacting member 70 for supplying and draining liquid as needed, in particular for maintaining a pressure equilibrium.

Liquid Level Detection Solutions

FIGS. 5A and 5B are sectional views through the assembled patient interface 26 taken along a section line perpendicular to that of FIG. 4. A first solution for monitoring the fluid level within the interface 26 comprises a pair of conductive pads 120 mounted to an inner wall of the eye-contacting member 70, such as diametrically across from one another (of course, the conductors could be mounted at other locations). Circuitry associated with the conducting pads 120 is not shown but would include a current sensor for detecting any current passing between the pads 120. FIG. 5A shows the liquid 110 filling the chamber 112. In this configuration, which is preferred for normal laser operation, a current may be passed through the liquid between the conducting pads 120, thus closing the associated circuit. On the other hand, when the level of the liquid 110 drops in the chamber 112, as seen in FIG. 5B, an air gap exists between the conducting pads 120, thus preventing current flow between the pads. Consequently, the current sensor communicates with the control electronics 54 and if the laser is in use, shuts it down. A pair of spaced conducting pads 120 may be mounted at the same level as shown, or two or more pairs and associated circuits may be included to provide indicators for multiple fluid levels. In an alternative configuration, the sensing pads 120 may be calibrated to measure capacitance which is altered when the fluid drops low enough to lose contact with the pads.

FIGS. 6A and 6B illustrate a second solution for optically monitoring the fluid level within the patient interface 26. More particularly, a light emitting source 130 is provided within the patient interface 26 or above it so that it shines downward at an angle through the lens 62 and into the liquid 110 in the chamber 112. When the light from the source 130 hits the surface of the liquid 110, it refracts as shown. A position detector 132 mounted to the inner wall of the eye-contacting member 70 senses the position of the refractive light. For a high liquid level, as seen in FIG. 6A, the angle of refraction causes the light to hit the position detector 132 relatively high up. On the other hand, when the liquid level drops, as seen in FIG. 6B, the angle of refraction is altered such that the light reaches the position detector 132 lower down, thus indicating an unacceptable loss of liquid. At some point the position detector 132 communicates with the control electronics 54 and if the laser is in use, shuts it down. The light position detector 132 could be either a continuous position detector to sense all fluid levels continuously, or may be constructed with discrete detectors to monitor specific levels (e.g., normal and low).

FIGS. 7A and 7B illustrate the patient interface 26 with a matched pair of acoustic emitter 140 and sensor 142 integrated therein. In particular, the emitter 140 and sensor 142 are mounted to the inner wall of the frustoconical body 80 diametrically across from one another. When the liquid 110 is at a high level in the chamber 112, acoustic signals from the emitter 140 are received by the sensor 142 through the fluid therebetween. After the liquid level drops, as seen in FIG. 7B, the sound waves from the emitter 140 take on a much different character passing through the air gap to the sensor 142. Fluid loss may also be detected by the changing character of the acoustic signature induced by a changing fluid volume, even before the level of the liquid descends below either the emitter 140 or the sensor 142. The emitter 140 and sensor 142 may be integrated into the frustoconical body 80 of the eye-contact member 70, or may be provided as separate components either mounted to the body or introduced into the liquid 110 from above.

FIGS. 8A and 8B shows the patient interface 26 having a small orifice 150 through the wall of the body 80. A nipple (not numbered) leading from the orifice 150 connects to a vacuum line 152. A slight vacuum can be applied through the vacuum line 152 and thus to the orifice 150. When the orifice 150 is covered by fluid, such as seen in FIG. 8A, surface tension will prevent the fluid from passing through the orifice, which results in a full vacuum. The magnitude of the vacuum pressure is sensed and a full vacuum means there is sufficient fluid in the chamber 112. Alternatively, when the level of the liquid 110 drops below the orifice 150, the slight vacuum will pull any residual fluid and air through the orifice 150, thus significantly lowering the magnitude of the vacuum or negative pressure from loss of resistance. If the laser is operating it is then shut off. The diameter of the orifice 150 is extremely small such that surface tension of the liquid prevents aspiration through the orifice when a low vacuum is applied, but allows free flow of air when the fluid level drops below the orifice. A number of orifices 150 can be provided in various positions around the body 80 to reduce false-negative conditions and/or provide sensing at multiple fluid levels.

Finally, an indirect method for monitoring the fluid level 110 within the patient interface may be incorporated into the patient interface suction system. FIG. 9 is a schematic of suction circuits connected to the patient interface 26, and illustrates the eye E below the patient interface including the upper member 76 and eye-contacting member 70.

The patient interface 26 couples to the first suction conduit 74a and second suction conduit 74b. The first suction conduit 74a extends from the suction ring 72 (see FIG. 4) to a vacuum source such as an eye retention structure vacuum pump 200. The suction conduit 74a couples the first fluid collector 202 to the patient interface 26 to receive fluid therefrom. A first fluid stop 204 couples to an outlet of the first collector 202 and includes a float valve or porous structure to pass a gas such as air and inhibit flow of a liquid or viscous material so as to stop substantially the flow of the liquid or viscous. A suction vacuum regulator 206 along first suction conduit 74a provides a regulated amount of pressure to eye E with the suction ring, for example suction pressure between about 300 and 500 mm Hg (millimeters Mercury), for example. The outlet of the suction vacuum regulator 206 is coupled to the vacuum pump 200 which is coupled to control electronics 54 with communication paths 60.

The second suction conduit 74b extends from the patient interface 26 to a vacuum source such as dock vacuum pump 210. The second suction conduit 74b provides suction to the interface between the upper member 76 and the eye-contacting member 70, and clamps the two together. Suction conduit 74b extends to a second fluid collector 212 and then to a second fluid stop 214 which contains a porous structure or float valve to inhibit flow of a liquid or viscous material and substantially stop the flow therethrough. The components within dashed area 216 form a liquid optics interface (LOI). The second fluid stop 214 couples to a dock monitor 215, which can be positioned along second suction conduit 74b in order to monitor suction for coupling upper member 76 to eye-contacting member 70. Suction monitor 215 comprising a pressure sensor is positioned along the second suction conduit 74b downstream of the second fluid stop 214 and a dock solenoid valve 216. The pressure sensor 215 can be coupled to control electronics 54 via the communication paths 60, as described herein. The pressure sensor 215 preferably comprises a transducer responsive to pressure of the suction conduit 74b. The suction solenoid valve 216 is coupled to control electronics 54, and the second suction conduit 74b may include another suction line monitor 217 to monitor suction downstream of suction solenoid valve 216. The suction line monitor 217 preferably couples to an inlet of the vacuum pump 210, which is also connected to the control electronics 54.

The third conduit 90 connected to the patient interface 26 (see FIG. 4) leads to a suction monitor 220 and then to a suction solenoid valve 222. The suction monitor 220 keeps track of the section level within the suction ring 72 and is coupled to control electronics 54 via the communication paths 60.

To indirectly sense liquid loss, a flow sensor 230 is introduced in the first suction conduit 74a in series between a suction solenoid valve 232 and the vacuum regulator 206. The flow sensor 230, which may be a gas flow meter, monitors gas flow within the first suction conduit 74a, and provides an alternative method for detecting major suction loss as well as slow leaks by utilizing a sensor of high sensitivity. A loss of liquid in the patient interface 26 may be caused by displacement between the interface and the patient's eye, which suddenly alters the gas flow into the suction ring 72. That is, when the suction ring 72 is engaged with the eye there is very little gas flow, while a disconnect suddenly allows air to be sucked into the suction conduit 74a. This can be sensed by the flow sensor 230 which is in communication with control electronics 54 which may shut the system down if the laser is operational. A high enough flow sensitivity also will detect small leaks which could ultimately lead to a major liquid loss.

The coupling lines as described herein may comprise lines for fluidic coupling known to a person of ordinary skill in the art and may comprise one or more of tubing, flexible tubing, rigid tubing, plastic tubing, metal tubing or manifolds, for example. The containers as described herein may comprise similar materials and can be constructed by a person of ordinary skill in the art based on the teachings provided herein.

A preferred laser cataract surgery using the aforementioned system is done by connecting the patient's eye with the laser system via a liquid-filled patient interface. The lower part of the patient interface attaches to the patient's eye by applying a vacuum over a ring-shaped area. The patient interface is then filled with a suitable sterile liquid (e.g., a sterile buffered saline solution (BSS)) interior to this ring, so that the sterile liquid is in direct contact with the patient's cornea. The patient is then moved with the chair to a position where the top part of the patient interface can be attached to an overhanging laser system by pulling vacuum over a second area, also with the shape of a ring. The sterile liquid is also in direct contact with the laser system's optics and the becomes part of the optical system of the instrument, interfacing the optical hardware with the patient's eye.

During treatment, the laser energy is transmitted into the patient's eye thought the sterile liquid contained in the patient interface. Precise positioning of the laser beam in the human eye is very important and the system optics, interface liquid and eye media are taken into consideration by the system software.

If during treatment, the liquid level within the interface to the patient were to decrease, the optics for the laser would be affected because air has a smaller index of refraction, perhaps causing harm to the patient. This situation could be caused by patient movement displacing the patient interface components such that sterile liquid enters the various vacuum conduits. Thus, the various techniques for detecting liquid loss within the patient interface 26 alert the physician/technician or system electronics to a possible catastrophic situation and corrective action can be quickly taken.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system for detecting loss of liquid in a patient interface of a laser eye surgery system having a diagnostic and interventional unit with a cutting laser for performing the laser eye surgery, and control electronics for the cutting laser, the system comprising:
   an optical coherence tomography (OCT) imaging system configured to image an eye of a patient;
   a patient interface including a rigid body and a lower suction ring on a lower end thereof for engaging the eye of the patient, wherein the patient interface is configured to be coupled to the diagnostic and interventional unit, the rigid body defining a throughbore for passage of a cutting laser beam of the cutting laser, and wherein the throughbore defines a fluid chamber configured to contain a fluid that provides a transmissive media for the cutting laser beam passing through the throughbore;
   a sensor separate from the OCT imaging system and mounted so as to be in communication with the fluid chamber, the sensor capable of detecting a fluid level within the fluid chamber; and
   a control and communication circuit that receives input from the sensor and provides output regarding a low fluid level within the chamber to the control electronics of the cutting laser.

2. The system of claim 1, wherein the rigid body defines a conical field of view from an upper end to the lower suction ring, and wherein the fluid chamber extends outward from the conical field of view and the sensor is mounted on the rigid body outside of the conical field of view.

3. The system of claim 1, wherein the sensor comprises a pair of conductive pads mounted to an inner surface of the rigid body, and the system includes circuitry associated with the conducting pads including a current sensor for detecting any current passing between the pads.

4. The system of claim 3, wherein there are at least two pairs of the conductive pads at different elevations within the rigid body for detecting any current passing between the pairs of pads at the different elevations.

5. The system of claim 1, wherein the sensor comprises a position detector mounted to an inner surface of the rigid body and the system includes a light emitting source positioned to shine downward at an angle through the fluid chamber such that light from the source hits the surface of the liquid and refracts, and the position detector senses the position of the refractive light which indicates a fluid level within the chamber.

6. The system of claim 1, wherein the sensor comprises a matched pair of an acoustic emitter and a sensor mounted to an inner surface of the rigid body and diametrically across from one another.

7. The system of claim 1, wherein the sensor comprises a small orifice extending through a wall of the rigid body and connected to a vacuum line and a pressure sensor therefor, wherein the orifice is sized such that when an opening thereof to the fluid chamber is covered by fluid, surface tension will prevent the fluid from passing through the orifice, which results in a maximum vacuum magnitude, and when the opening is exposed to air the air flows through the vacuum line and the vacuum magnitude drops below the maximum.

8. The system of claim 1, further including an optical lens mounted within the rigid body and defining an upper extent of the fluid chamber.

9. The system of claim 1, further including an optical lens mounted within the rigid body and defining an upper extent of the fluid chamber, and wherein the light emitting source is mounted above the optical lens and within the rigid body.

10. The system of claim 1, wherein the lower suction ring defines two annular walls having a space therebetween, the system further including:
   a conduit in fluid communication with the space between the two annular walls;
   a vacuum pump configured to apply a vacuum to the space between the two annular walls of the lower suction ring via the conduit to secure the lower suction ring to a surface of the eye; and
   a flow sensor disposed in a fluid path between the space and the vacuum pump, the flow sensor detecting a flow of air in the conduit caused by a disconnection of the patient interface from the surface of the eye indicating a loss of the fluid in the fluid chamber.

11. A method for detecting loss of liquid in a patient interface of a laser eye surgery system having a diagnostic and interventional unit with a cutting laser for performing the laser eye surgery, and control electronics for the laser, the method comprising:
   providing an optical coherence tomography (OCT) system for imaging an eye of a patient;
   coupling a patient interface to the diagnostic and interventional unit;
   engaging a suction ring of the patient interface to the eye of the patient, the patient interface including a rigid body and the suction ring on a lower end thereof for engaging an eye of a patient, the rigid body defining a throughbore for passage of a cutting laser beam of the cutting laser, and wherein the throughbore defines a fluid chamber;
   filling the fluid chamber within the rigid body with fluid that provides a transmissive media for the cutting laser beam passing through the throughbore;
   sensing a fluid level within the fluid chamber using a sensor separate from the OCT imaging system and mounted so as to be in communication with the fluid chamber; and
   transmitting information from the sensor to a control and communication circuit; and
   the control and communication circuit providing output regarding a low fluid level within the chamber to the control electronics of the laser.

12. The method of claim 11, wherein the rigid body defines a conical field of view from an upper end to the lower suction ring, and wherein the fluid chamber extends outward from the conical field of view and the sensor is mounted on the rigid body outside of the conical field of view.

13. The method of claim 11, wherein the sensor comprises a pair of conductive pads mounted to an inner surface of the rigid body, and the system includes circuitry associated with the conducting pads including a current sensor for detecting any current passing between the pads, and the method includes frequently attempting to pass current between the conductive pads.

14. The method of claim 13, wherein there are at least two pairs of the conductive pads at different elevations within the rigid body for detecting any current passing between the pairs of pads at the different elevations, and the method includes frequently attempting to pass current between the pairs of conductive pads.

15. The method of claim 11, wherein the sensor comprises a position detector mounted to an inner surface of the rigid body and the system includes a light emitting source positioned to shine downward at an angle through the fluid chamber such that light from the source hits the surface of the liquid and refracts, and the position detector senses the position of the refractive light which indicates a fluid level within the chamber, and the method includes frequently activating the light emitting source and monitoring the position detector.

16. The method of claim 15, further including an optical lens mounted within the rigid body and defining an upper extent of the fluid chamber, and wherein the light emitting source is mounted above the optical lens and within the rigid body.

17. The method of claim 11, wherein the sensor comprises a matched pair of an acoustic emitter and a sensor mounted to an inner surface of the rigid body and diametrically across from one another, and the method includes frequently activating the acoustic emitter and sensor to detect a low fluid level.

18. The method of claim 11, wherein the sensor comprises a small orifice extending through a wall of the rigid body and connected to a vacuum line and a pressure sensor therefor, wherein the orifice is sized such that when an opening thereof to the fluid chamber is covered by fluid, surface tension will prevent the fluid from passing through the orifice, which results in a maximum vacuum magnitude, and when the opening is exposed to air the air flows through the vacuum line and the vacuum magnitude drops below the maximum, and the method includes continuously monitoring the vacuum magnitude.

19. The method of claim 11, further including an optical lens mounted within the rigid body and defining an upper extent of the fluid chamber.

20. A system for detecting loss of liquid in a patient interface of a laser eye surgery system having a diagnostic and interventional unit with a cutting laser for performing the laser eye surgery, and control electronics for the cutting laser, the system comprising:
   a patient interface including a rigid body and a lower suction ring on a lower end thereof for engaging an eye of a patient, wherein the patient interface is configured to be coupled to the diagnostic and interventional unit, the rigid body defining a throughbore for passage of a cutting laser beam of the cutting laser, wherein the throughbore defines a fluid chamber configured to contain a fluid that provides a transmissive media for the cutting laser beam passing through the throughbore, and wherein the lower suction ring defines two annular walls having a space therebetween;
a conduit in fluid communication with the space between the two annular walls;
a vacuum pump configured to apply a vacuum to the space between the two annular walls of the lower suction ring via the conduit to secure the lower suction ring to a surface of the eye;
a sensor disposed in a fluid path between the space and the vacuum pump, the sensor detecting a flow of air in the conduit caused by a disconnection of the patient interface from the surface of the eye indicating a loss of the fluid in the fluid chamber; and
a control and communication circuit that receives input from the sensor and provides output regarding a loss of fluid within the chamber to the control electronics of the cutting laser.

* * * * *